US010441407B2

(12) United States Patent
Sethna

(10) Patent No.: US 10,441,407 B2
(45) Date of Patent: Oct. 15, 2019

(54) GUTTER FILLING STENT-GRAFT AND METHOD

(71) Applicant: Medtronic Vascular, Inc., Santa Rosa, CA (US)

(72) Inventor: Sohrab Sethna, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 269 days.

(21) Appl. No.: 15/096,939

(22) Filed: Apr. 12, 2016

(65) Prior Publication Data

US 2017/0290654 A1 Oct. 12, 2017

(51) Int. Cl.

| | |
|---|---|
| ***A61F 2/07*** | (2013.01) |
| *A61F 2/82* | (2013.01) |
| *A61F 2/945* | (2013.01) |
| *A61F 2/852* | (2013.01) |
| *A61F 2/06* | (2013.01) |

(52) U.S. Cl.

CPC ................ *A61F 2/07* (2013.01); *A61F 2/852* (2013.01); *A61F 2/945* (2013.01); *A61F 2002/061* (2013.01); *A61F 2002/077* (2013.01); *A61F 2002/826* (2013.01); *A61F 2210/0061* (2013.01); *A61F 2210/0085* (2013.01); *A61F 2250/0003* (2013.01); *A61F 2250/0023* (2013.01); *A61F 2250/0069* (2013.01)

(58) Field of Classification Search

CPC ........ A61F 2002/077; A61F 2250/0003; A61F 2250/0069

See application file for complete search history.

(56) References Cited

U.S. PATENT DOCUMENTS

| | | | |
|---|---|---|---|
| 5,693,088 A | 12/1997 | Lazarus | |
| 6,729,356 B1 | 5/2004 | Baker et al. | |
| 8,118,856 B2 | 2/2012 | Schreck et al. | |
| 2001/0027338 A1 | 10/2001 | Greenberg | |
| 2004/0098096 A1 | 5/2004 | Eton | |
| 2008/0294237 A1 | 11/2008 | Chu | |
| 2011/0257725 A1 | 10/2011 | Argentine et al. | |
| 2013/0331929 A1 | 12/2013 | Mitra et al. | |
| 2014/0100650 A1* | 4/2014 | Chobotov | A61F 2/07 623/1.35 |
| 2015/0209136 A1* | 7/2015 | Braido | A61F 2/2403 623/2.18 |
| 2016/0106537 A1* | 4/2016 | Christianson | A61F 2/2418 623/2.17 |

FOREIGN PATENT DOCUMENTS

WO WO2009/149294 12/2009

OTHER PUBLICATIONS

PCT/US2017/026936, The International Search Report and the Written Opinion of the International Searching Authority, dated Jun. 26, 2017, 15pgs.

* cited by examiner

*Primary Examiner* — Yashita Sharma
*Assistant Examiner* — Rebecca S Preston

(57) ABSTRACT

A primary stent-graft is deployed into a primary vessel to exclude an aneurysm. To maintain perfusion to a branch vessel covered by the primary stent-graft, a gutter filling stent-graft is deployed in parallel to the primary stent-graft. The gutter filling stent-graft includes a balloon that is pressurized and inflated by the patient's own blood thereby sealing any gutters formed around the gutter filling stent-graft. By sealing the gutters, the chance of type I endoleaks, migrations, and overall failure to exclude the aneurysm is minimized.

7 Claims, 8 Drawing Sheets

GUTTER FILLING STENT-GRAFT AND METHOD

BACKGROUND

Field

The present application relates to an intra-vascular device and method. More particularly, the present application relates to a device for treatment of intra-vascular diseases.

Description of the Related Art

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention. In one example, the stent-graft is anchored in a landing zone, sometimes called a neck, distal to a branch vessel and proximal to the aneurysm. In this manner, perfusion to the branch vessel is maintained while the aneurysm is excluded.

Challenges occur in patients with short or no-neck aneurysms. In these situations, parallel graph techniques have emerged as a viable option. More particularly, a primary stent-graft is deployed to exclude the aneurysm in parallel with a branch stent-graft which is used to maintain perfusion to the branch vessel. However, open channels, sometimes called gutters, between the primary stent-graft and the branch stent-graft are formed that allow blood to leak through the gutters. As the gutters are formed in the proximal seal region, the gutters lead to a greater chance of type I endoleaks, migrations, and overall failure to exclude the aneurysm.

SUMMARY

A primary stent-graft is deployed into a primary vessel to exclude an aneurysm. To maintain perfusion to a branch vessel covered by the primary stent-graft, a gutter filling stent-graft is deployed in parallel to the primary stent-graft. The gutter filling stent-graft includes a balloon that is pressurized and inflated by the patient's own blood using selective material permeability thereby sealing any gutters formed around the gutter filling stent-graft. By sealing the gutters, the chance of type I endoleaks, migrations, and overall failure to exclude the aneurysm is minimized.

BRIEF DESCRIPTION OF DRAWINGS

Common reference numerals are used throughout the drawings and detailed description to indicate like elements.

DETAILED DESCRIPTION

As an overview and in accordance with one embodiment, a primary stent-graft is deployed into a primary vessel to exclude an aneurysm. To maintain perfusion to a branch vessel covered by the primary stent-graft, a gutter filling stent-graft is deployed in parallel to the primary stent-graft. The gutter filling stent-graft includes a balloon that is pressurized and inflated by the patient's own blood using selective material permeability thereby sealing any gutters formed around the gutter filling stent-graft. By sealing the gutters, the chance of type I endoleaks, migrations, and overall failure to exclude the aneurysm is minimized.

Figure 1:
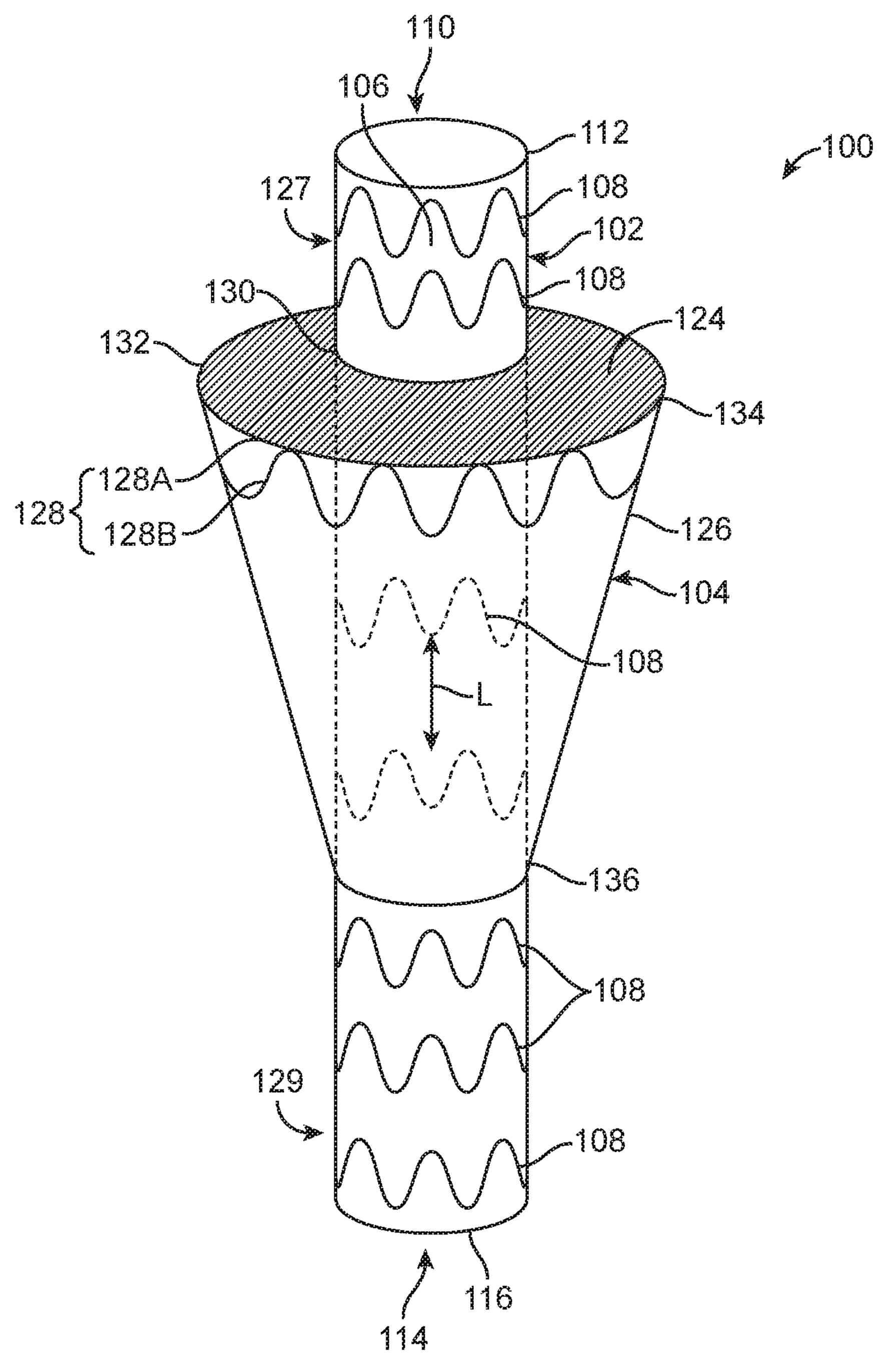
FIG. 1 is a perspective view of a gutter filling stent-graft in accordance with one embodiment.
Figure 2:
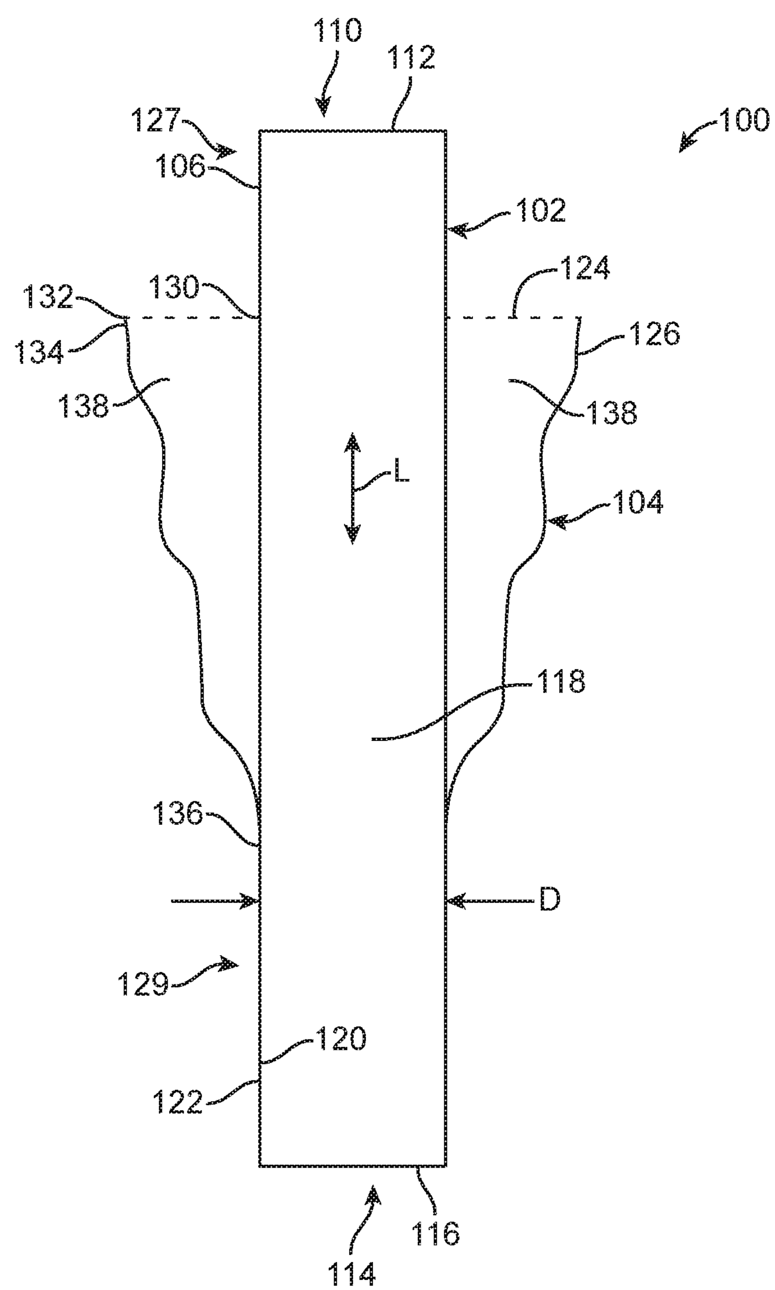
FIG. 2 is a cross-sectional view of the gutter filling stent-graft of FIG. 1 in accordance with one embodiment.
Figure 3:
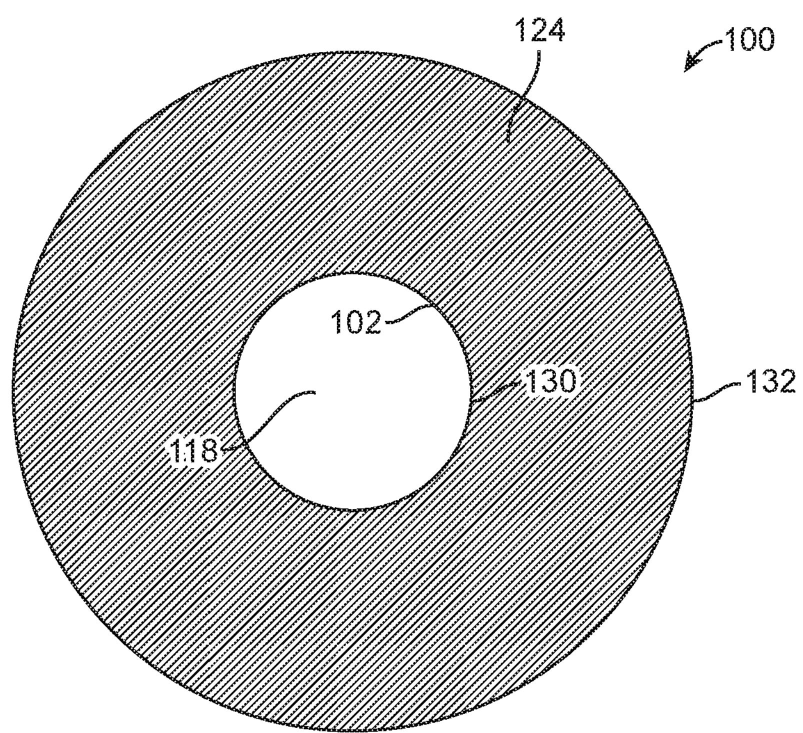
FIG. 3 is a top plan view of the gutter filling stent-graft of FIG. 1 in accordance with one embodiment.

Now in more detail, FIG. 1 is a perspective view of a gutter filling stent-graft 100 in accordance with one embodiment. FIG. 2 is a cross-sectional view of gutter filling stent-graft 100 of FIG. 1 in accordance with one embodiment. FIG. 3 is a top plan view of gutter filling stent-graft 100 of FIG. 1 in accordance with one embodiment.

Referring now to FIGS. 1, 2, and 3 together, gutter filling stent-graft 100 includes a main stent-graft 102 and a balloon 104 coupled to main stent-graft 102. Main stent-graft 102, sometimes called a branch stent-graft, includes a graft material 106 and one or more stent rings 108. Illustratively, stent rings 108 are self expanding structures, e.g., formed of nickel titanium alloy (nitinol), or other shaped memory material. In another embodiment, stent rings 108 are a balloon expandable material such as stainless steel or cobalt chromium. Stent rings 108 are not illustrated in all of the figures for clarity of presentation.

In accordance with this embodiment, graft material 106 includes a proximal opening 110 at a proximal end 112 of graft material 106 and a distal opening 114 at a distal end 116 of graft material 106.

Further, main stent-graft 102 includes a longitudinal axis L. A lumen 118 is defined by graft material 106, and generally by main stent-graft 102. Lumen 118 extends generally parallel to longitudinal axis L and between proximal opening 110 and distal opening 114 of main stent-graft 102.

As used herein, the proximal end of a prosthesis such as gutter filling stent-graft 100 is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the prosthesis is the end nearest the operator (the end nearest the handle), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the stent-graft and delivery system description may be consistent or opposite in actual usage.

Graft material 106, e.g., main stent-graft 102, is cylindrical having a substantially uniform diameter D. However, in other embodiments, graft material 106, e.g., main stent-graft 102, varies in diameter. Graft material 106 includes a cylindrical inner surface 120 and an opposite outer surface 122.

In one embodiment, graft material 106 is non-permeable, e.g., is polytetrafluoroethylene (PTFE), expanded polytetrafluoroethylene (ePTFE), or other non-permeable graft material. As graft material 106 is non-permeable, blood or other fluid does not pass through graft material 106.

Balloon 104 is coupled to outer surface 122 of main stent-graft 102. Balloon 104 includes a base 124, a balloon section 126, and an expansion member 128. A proximal portion 127 and a distal portion 129 of main stent-graft 102 are uncovered by balloon 104.

Base 124 is an annulus having an inner periphery 130 and an outer periphery 132. Inner periphery 130 is coupled to the outer surface 122 of main stent-graft 102, e.g., by stitching, adhesive, or other attachment means. Outer periphery 132 is coupled to a proximal end 134 of balloon section 126, e.g., by stitching, adhesive, or other attachment means. In accordance with this embodiment, base 124 is planar and perpendicular to longitudinal axis L of main stent-graft 102. However, in other embodiments, base 124 is non-planar, e.g., is a slanted surface.

Balloon section 126 extends between proximal end 134 and a distal end 136 of balloon section 126. In accordance with this embodiment, balloon section 126 is conical and so is sometimes called a conical section 126. More particularly, the diameter of balloon section 126 (in a plane perpendicular to longitudinal axis L) decreases as the distal distance from base 124 increases. Distal end 136 of balloon section 126 is coupled to the outer surface 122 of main stent-graft 102, e.g., by stitching, adhesive, or other attachment means.

In accordance with this embodiment, expansion member 128 includes a resilient ring 128A, e.g., a metallic ring, at outer periphery 132 of base 124 and at proximal end 134 of balloon section 126. In yet another embodiment, expansion member 128 includes a resilient stent ring 128B, e.g., a metallic stent ring, coupled to balloon section 126 at proximal end 134. Expansion member 128 is configured to expand upon deployment to thereby open base 124. Expansion member 128 includes ring 128A, stent-ring 128B, or both ring 128A and stent-ring 128B in various embodiments. Expansion member 128 is sometimes called a mechanical structure. Expansion member 128 is not illustrated in all of the figures for clarity of presentation.

In accordance with this embodiment, base 124 is permeable, e.g., fluid such as blood can readily pass through base 124. For example, base 124 is polyethylene terephthalate (PET), or other permeable graft material.

In contrast, balloon section 126 is non-permeable, e.g., is polytetrafluoroethylene (PTFE), expanded polytetrafluoroethylene (ePTFE), or other non-permeable graft material. As balloon section 126 is non-permeable, blood or other fluid does not pass through graft material 106.

Balloon 104 includes a balloon sack 138. More particularly, main stent-graft 102, base 124, and balloon section 126 define balloon sac 138. As described further below in reference to FIG. 4, blood through flows through permeable base 124 thus filling balloon sac 138 and inflating balloon 104 to expand balloon 104.

Figure 4:
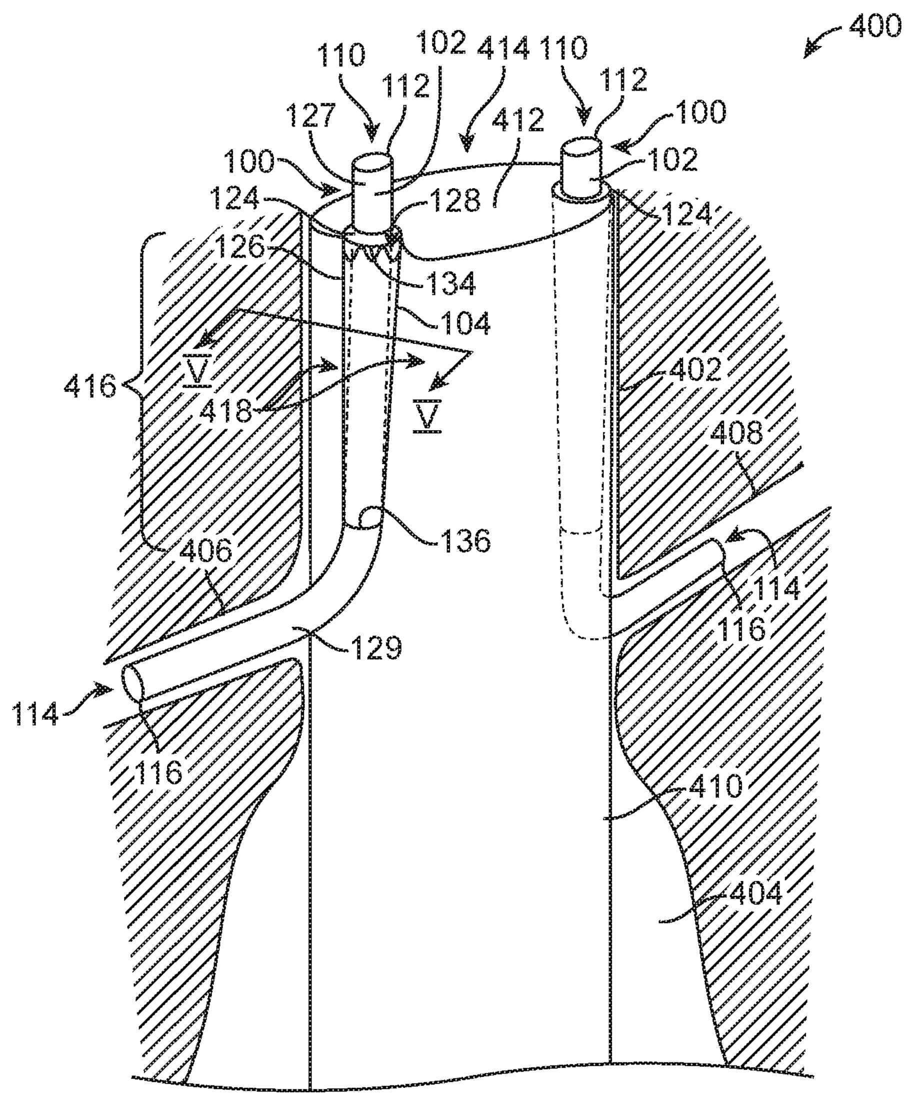
FIG. 4 is a partial cross-sectional view of a vessel assembly including the gutter filling stent-graft of FIGS. 1, 2, and 3 in accordance with one embodiment.

FIG. 4 is a partial cross-sectional view of a vessel assembly 400 including gutter filling stent-graft 100 of FIGS. 1, 2, and 3 in accordance with one embodiment. Referring now to FIG. 4, a primary vessel 402, e.g., the aorta, includes an aneurysm 404.

Emanating from primary vessel 402 is a first branch vessel 406 and a second branch vessel 408, sometimes called visceral branches of the abdominal aorta. The location of branch vessels 406, 408 vary from patient to patient. Examples of branch vessels include the renal arteries (RA).

An aneurysm exclusion stent-graft 410, sometimes called a second stent-graft or a primary (main) stent-graft, is deployed into primary vessel 402 to exclude aneurysm 404 using any one of a number of techniques well known to those of skill in the art. Aneurysm exclusion stent-graft 410 is deployed proximally of branch vessels 406, 408 and thus covers and occludes branch vessels 406, 408. In one embodiment, aneurysm exclusion stent-graft 410 includes one or more stents which are not illustrated in FIG. 4 for purposes of clarity.

For example, aneurysm 404 is a short or no neck aneurysm having little to no healthy tissue between branch vessels 406, 408 and aneurysm 404. Accordingly, aneurysm exclusion stent-graft 410 is deployed proximally of branch vessels 406, 408 and into healthy tissue. Once anchored within primary vessel 402, blood flows through a lumen 412 of aneurysm exclusion stent 410 thus excluding aneurysm 404.

To maintain perfusion to branch vessels 406, 408, two gutter filling stent-grafts 100 are deployed in parallel to aneurysm exclusion stent-graft 410. Although two branch vessels 406, 408 and two gutter filling stent-grafts 100 are illustrated in FIG. 4 and discussed herein, in another embodiment, only a single branch vessel is covered by aneurysm exclusion stent-graft 410 and a single gutter filling stent-graft 100 is deployed to maintain perfusion to the single branch vessel. For simplicity, the deployment and operation of a single gutter filling stent-graft 100 is described below. However, in light of this disclosure, those of skill in the art will understand that the description is equally applicable to the second gutter filling stent-graft 100 and generally to a plurality of gutter filling stent-grafts 100. Although an abdominal aortic aneurysm (AAA) is discussed, parallel grafting techniques using gutter filling stent-graft 100 are used for treatment of challenging thoracic and iliac arteries in other embodiments.

Proximal opening 110 of gutter filling stent-graft 100 is deployed proximally to a proximal opening 414 of aneurysm exclusion stent-graft 410. Distal opening 114 is deployed within branch vessel 406. Accordingly, blood flows from primary vessel 402, enters into proximal opening 110, through lumen 118, exits distal opening 114, and into branch vessel 406. In this manner, gutter filling stent-graft 100 maintains perfusion of branch vessel 406.

Gutter filling stent-graft 100 is deployed in parallel with aneurysm exclusion stent-graft 410 such that balloon 104 is located in an overlap area 416 of parallel graft interaction of gutter filling stent-graft 100 and aneurysm exclusion stent-graft 410. Gutter filling stent-graft 100 is deployed prior to, simultaneously, or subsequent to deployment of aneurysm exclusion stent-graft 100 using various delivery devices in different embodiments.

Figure 5:
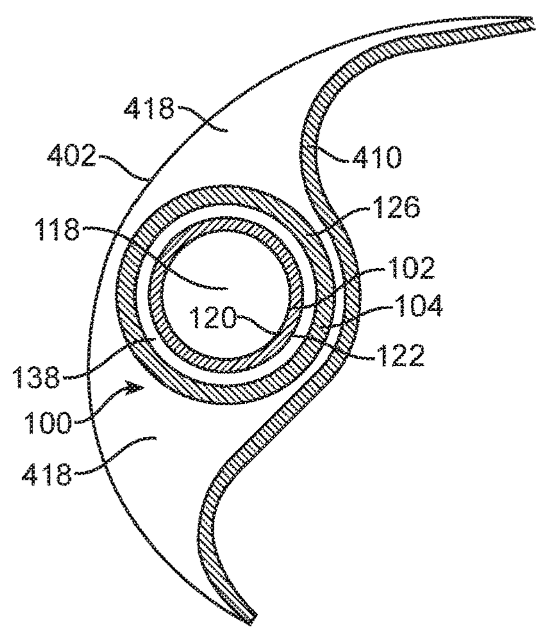
FIG. 5 is a cross-sectional view along the line V-V of FIG. 4 of the gutter filling stent-graft at an initial stage of deployment.

FIG. 5 is a cross-sectional view along the line V-V of FIG. 4 of gutter filling stent-graft 100 at an initial stage of deployment. Referring to FIGS. 4 and 5 together, aneurysm exclusion stent-graft 410 generally conforms to primary vessel 402 and gutter filling stent-graft 100. However, aneurysm exclusion stent-graft 410 does not conform perfectly such that gutters 418 are formed around gutter filling stent-graft 100. Gutters 418 are open channels extending generally parallel to longitudinal axis L of main stent-graft 102. Gutters 418 are open spaces defined by primary vessel 402, gutter filling stent-graft 100, and aneurysm exclusion stent-graft 410. Note balloon sac 138 is empty upon initial deployment such that balloon section 126 is directly adjacent to and collapsed upon graft material 106 of main stent-graft 102.

Upon deployment, expansion member 128 opens base 124 and blood flows through base 124 and into balloon 104 to fill balloon sac 138. More particularly, base 124 is permeable and held open by expansion member 128. As base 124 is placed within the path of blood flow, blood flows through base 124.

However, graft material 106 and balloon section 126 are non-permeable. Accordingly, the blood that flows through base 124 is held in balloon sac 138 by graft material 106 and balloon section 126. This causes balloon 104 to expand, sometimes called inflate or balloon, as discussed further below in reference to FIG. 6. In this manner, selective material permeability is used to expand balloon 104.

Figure 6:
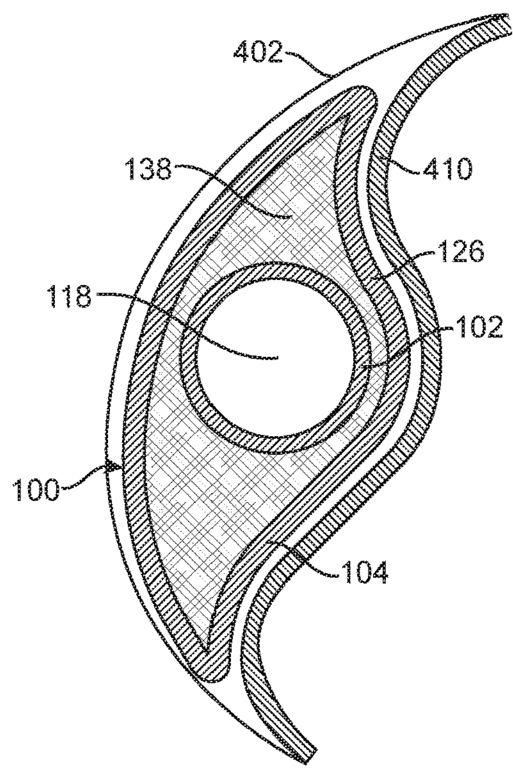
FIG. 6 is a cross -sectional view along the line V-V of FIG. 4 of the gutter filling stent-graft at a later stage of deployment.

FIG. 6 is a cross -sectional view along the line V-V of FIG. 4 of gutter filling stent-graft 100 at a later stage of deployment. Referring to FIGS. 4, 5, and 6 together, blood flow through base 124 causes balloon section 126 to expand outward and into gutters 418. In one embodiment, balloon section 126 includes loose graft material, sometimes called a balloon of fabric, that is forced into gutters 418 by the blood flow.

Once fully expanded, balloon 104 seals (eliminates) gutters 418 thus preventing blood leakage through gutters 418. Over time, due to the coagulation properties of blood, first the permeable base 124 will coagulate and prevent further blood flow. Eventually, all the trapped blood within balloon section 126 will also coagulate. This action effectively seals gutters 418, sometimes called gutter regions, using the patient's own blood pressure and the thrombogenic properties of blood. By sealing gutters 418, the chance of Type I endoleaks, migration, and overall failure to exclude aneurysm 404 is minimized.

Figure 7:
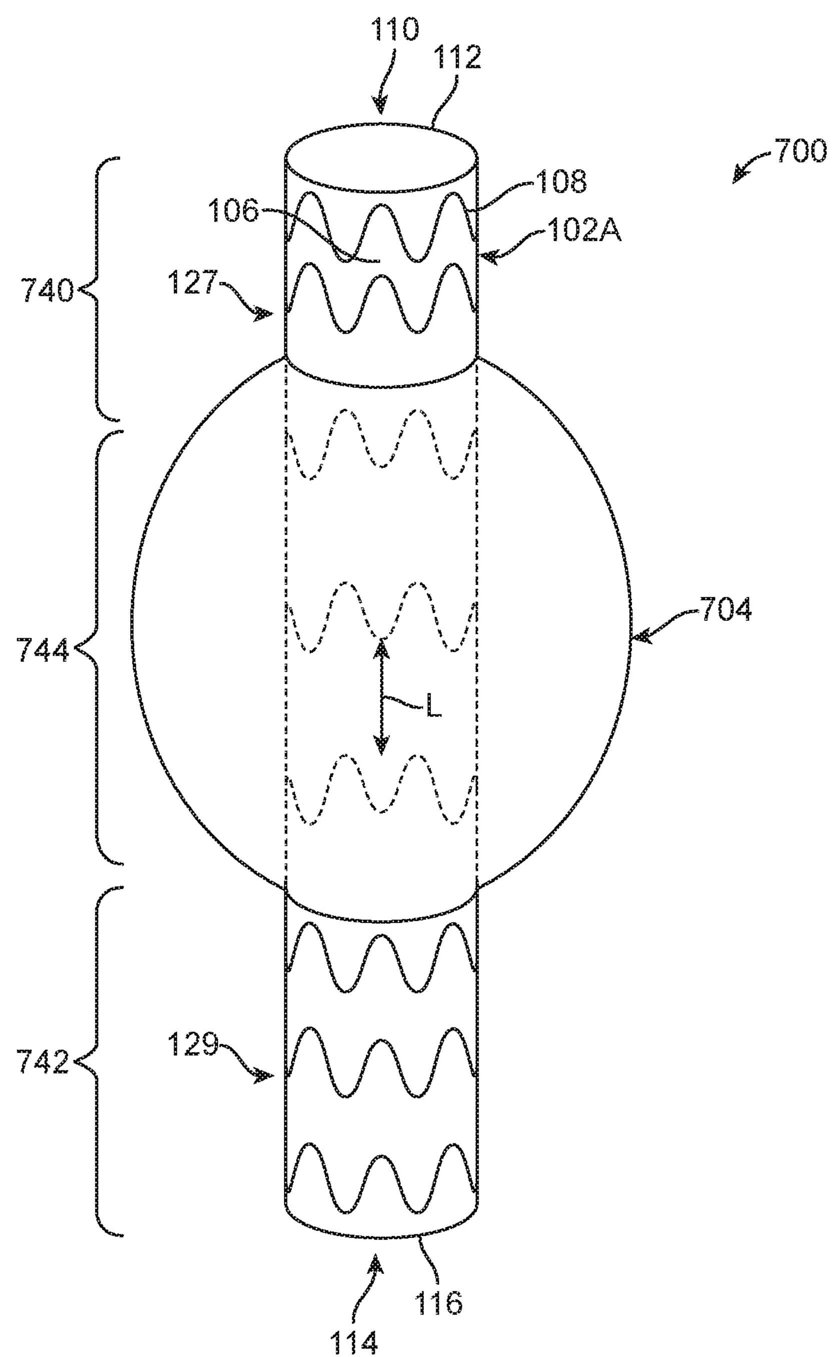
FIG. 7 is a perspective view of a gutter filling stent-graft in accordance with another embodiment.
Figure 8:
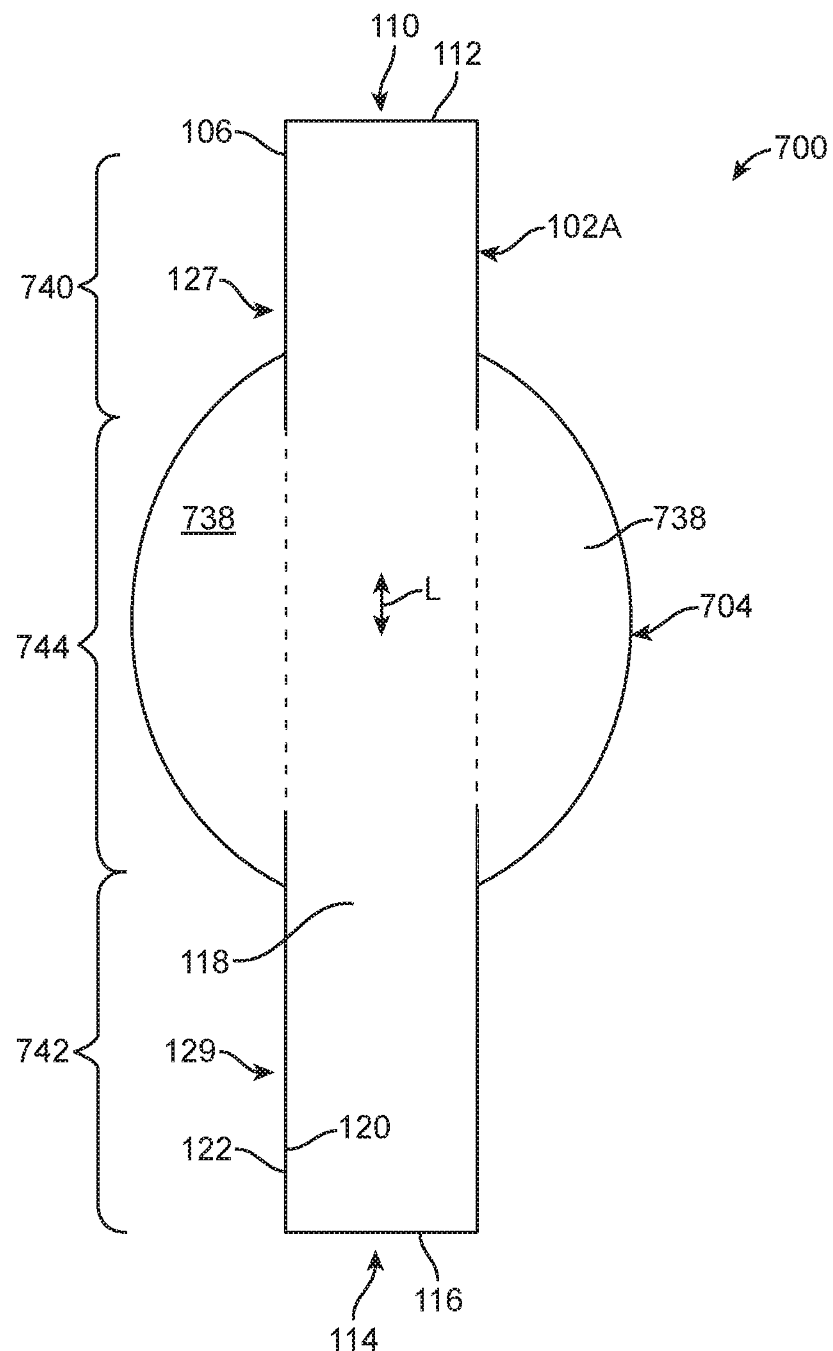
FIG. 8 is a cross-sectional view of the gutter filling stent-graft of FIG. 7 in accordance with one embodiment.

FIG. 7 is a perspective view of a gutter filling stent-graft 700 in accordance with another embodiment. FIG. 8 is a cross-sectional view of gutter filling stent-graft 700 of FIG. 7 in accordance with one embodiment. Gutter filling stent-graft 700 of FIGS. 7 and 8 is similar to gutter filling stent-graft 100 of FIGS. 1 and 2 and only the significant differences are discussed below.

Referring now to FIGS. 7 and 8 together, gutter filling stent-graft 700 includes a main stent-graft 102A and a balloon 704 coupled to outer surface 122 of main stent-graft 102A. Graft material 106 of main stent-graft 102A includes a proximal section 740, a distal section 742 and a middle section 744 between and coupled to proximal section 740 and distal section 742. Proximal and distal sections 740, 742 are non permeable materials such as those described above. Middle section 744 is configured to allow blood to pass therethrough.

In accordance with this embodiment, middle section 744 of graft material 106 is a permeable material such as those discussed above. Middle section 744 is attached to proximal and distal sections 740, 742, e.g., by stitching, adhesive, or other attachment means.

Balloon 704 is coupled to proximal section 740 and distal section 742. Balloon 704 is disposed around middle section 744. Accordingly, a balloon sac 738 is defined by main stent-graft 102A and balloon 704. Balloon sac 738 is in fluid communication with lumen 118 of main stent-graft 102A through middle section 744.

During use, referring now to FIGS. 4, 5, 7, and 8 together, gutter filling stent-graft 700 is deployed in parallel with an aneurysm exclusion stent-graft 410. In accordance with this embodiment, balloon 704 is deployed in the same location as balloon 104 as illustrated in FIGS. 4 and 5.

Blood flows through lumen 118, through middle section 744, and into balloon sac 738. This expands balloon 704 into and seals gutters 418 in a manner similar to that discussed above regarding balloon 104 and gutters 418. In this manner, selective material permeability is used to expand balloon 704.

Figure 9:
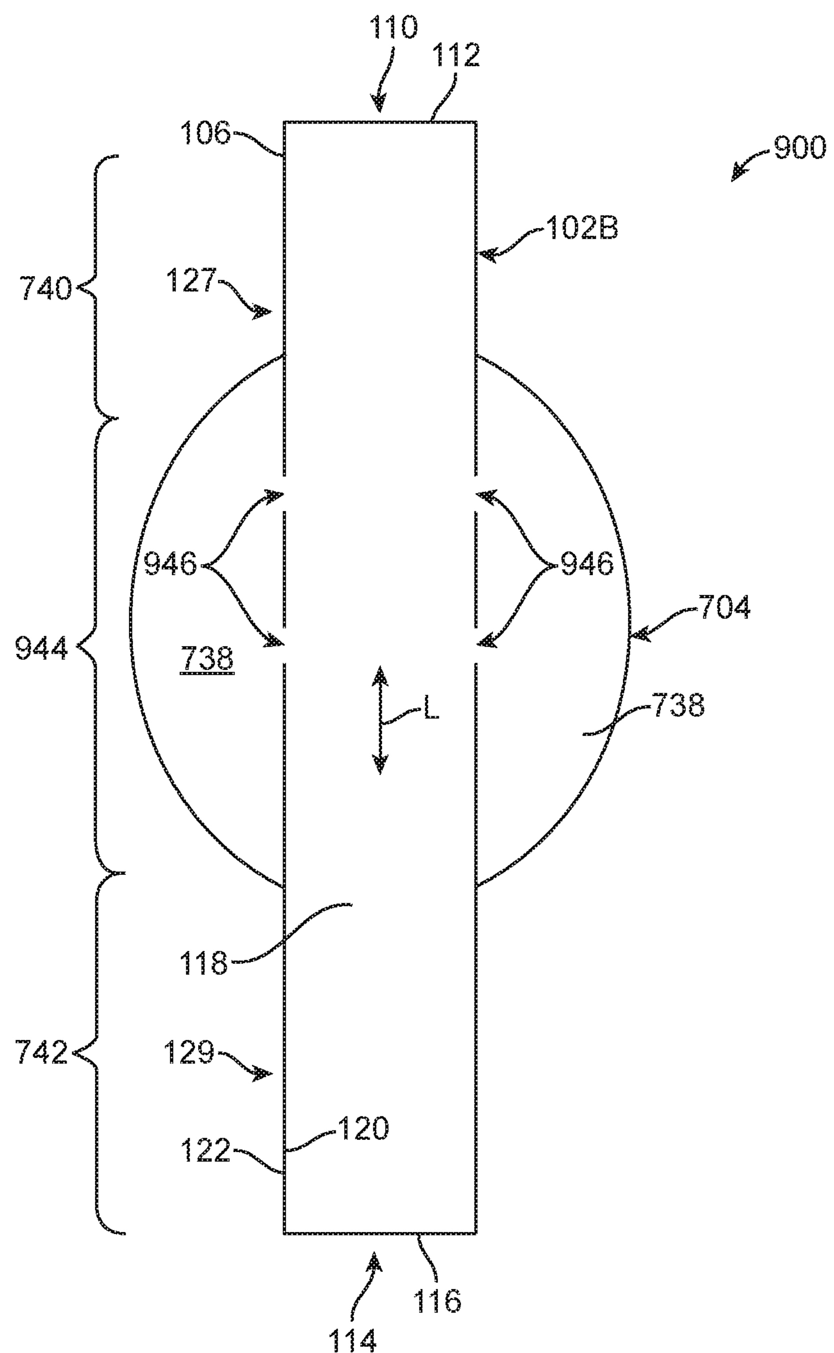
FIG. 9 is a cross-sectional view of a gutter filling stent-graft in accordance with yet another embodiment.

FIG. 9 is a cross-sectional view of a gutter filling stent-graft 900 in accordance with yet another embodiment. Gutter filling stent-graft 900 of FIG. 9 is similar to gutter filling stent-graft 700 of FIGS. 7 and 8 and only the significant differences are discussed below.

Referring now to FIG. 9, gutter filling stent-graft 900 includes a main stent-graft 102B and a balloon 704 coupled to outer surface 122 of main stent-graft 102B. Graft material 106 of main stent-graft 102B includes a proximal section 740, a distal section 742 and a middle section 944 between and coupled to proximal section 740 and distal section 742. Proximal and distal sections 740, 742 are non permeable materials such as those described above. Middle section 944 is configured to allow blood to pass therethrough.

In accordance with this embodiment, middle section 944 of graft material 106 is a non-permeable material such as those discussed above. However, middle section 944 includes one or more apertures 946, sometimes called openings or holes, therein. Middle section 944 is attached to proximal and distal sections 740, 742, e.g., by stitching, adhesive, or other attachment means. In yet another embodiment, middle section 944, proximal section 740, and distal section 742 are sections of a single integral non permeable graft material having apertures 946 formed in the area of middle section 944.

Balloon 704 is coupled to proximal section 740 and distal section 742. Balloon 704 is disposed around middle section 944. Accordingly, a balloon sac 738 is defined by main stent-graft 102B and balloon 704. Balloon sac 738 is in fluid communication with lumen 118 of main stent-graft 102B through apertures 946 in middle section 944.

During use, referring now to FIGS. 4, 5 and 9 together, gutter filling stent-graft 900 is deployed in parallel with an aneurysm exclusion stent-graft 410. In accordance with this embodiment, balloon 704 is deployed in the same location as balloon 104 as illustrated in FIGS. 4 and 5.

Blood flows through lumen 118, through middle section 944, and into balloon sac 738. More particularly, blood flows through apertures 946 and into balloon sac 738. This expands balloon 704 into and seals gutters 418 in a manner similar to that discussed above regarding balloon 104 and gutters 418.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A graft assembly comprising:

a primary stent-graft in parallel with a gutter filling stent-graft;

the gutter filling stent-graft comprising:

a main stent-graft comprising non-permeable graft material comprising an inner surface and an outer surface, the inner surface defining a lumen within the graft material; and a balloon coupled to the graft material at the outer surface, the balloon comprising:

a base comprising permeable material, the base being perpendicular to a longitudinal axis of the main stent-graft;

a balloon section coupled to the base, the balloon section comprising non-permeable material; and a single expansion member configured to expand the base, the single expansion member coupled to either an outer periphery of the base or an end of the balloon section which is coupled to the base, wherein the main stent-graft, the base, and the balloon section define an inflatable balloon sac of the balloon.

2. The graft assembly of claim 1 wherein the balloon section is conical such that a diameter of the balloon section decreases as the distal distance from the base increases.

3. The graft assembly of claim 1 wherein the single expansion member comprises a resilient ring at the outer periphery of the base.

4. The graft assembly of claim 1 wherein the single expansion member comprises a stent-ring.

5. The graft assembly of claim 1 wherein the base comprises an annulus comprising an inner periphery coupled to the main stent-graft and the outer periphery coupled to the balloon section.

6. The graft assembly of claim 1 wherein the single expansion member consists of a resilient ring at the outer periphery of the base.

7. The graft assembly of claim 1 wherein the single expansion member consists of a stent-ring at the end of the balloon section which is coupled to the base.

* * * * *